(12) United States Patent
Dahl et al.

(10) Patent No.: US 7,699,858 B2
(45) Date of Patent: Apr. 20, 2010

(54) SURGICAL FASTENER

(76) Inventors: Terry Dahl, 3635 San Pablo La., Santa Barbara, CA (US) 93105; Stan Needle, 764 W. Lois Ct., Lousiville, CO (US) 80027; Frank Patterson, 18 Juniper Ridge Rd., Exeter, NH (US) 03833; Hugh H. Trout, 8218 Wisconsin Ave., Suite 204, Bethesda, MD (US) 20814

( * ) Notice: Subject to any disclaimer, the term of this patent is extended or adjusted under 35 U.S.C. 154(b) by 939 days.

(21) Appl. No.: 11/038,406

(22) Filed: Jan. 21, 2005

(65) Prior Publication Data
US 2005/0187569 A1 Aug. 25, 2005

Related U.S. Application Data

(60) Provisional application No. 60/537,888, filed on Jan. 22, 2004, provisional application No. 60/538,242, filed on Jan. 23, 2004.

(51) Int. Cl.
*A61B 17/08* (2006.01)
(52) U.S. Cl. ..................................... 606/151
(58) Field of Classification Search ............. 606/200, 606/219, 151, 155, 213
See application file for complete search history.

(56) References Cited

U.S. PATENT DOCUMENTS

| | | | |
|---|---|---|---|
| 5,693,067 A * | 12/1997 | Purdy | 606/200 |
| 6,280,457 B1 * | 8/2001 | Wallace et al. | 606/200 |
| 2001/0047181 A1 * | 11/2001 | Ho et al. | 606/157 |
| 2002/0010411 A1 * | 1/2002 | Macoviak et al. | 604/8 |
| 2005/0107823 A1 * | 5/2005 | Leone et al. | 606/200 |

* cited by examiner

*Primary Examiner*—(Jackie) Tan-Uyen T. Ho
*Assistant Examiner*—Gregory Anderson

(57) ABSTRACT

A surgical fastener having a first and a second end for securing at least two surfaces together. The surgical fastener has a first configuration where the fastener is coupled to a restraining device that holds the fastener and a second configuration wherein the fastener is released from said restraining device. The second configuration has a substantially spiral shape and is spring biased along an axis perpendicular to the surfaces that it is securing. The surgical fastener also includes a rib that extends along the longitudinal axis of the fastener.

2 Claims, 9 Drawing Sheets

SURGICAL FASTENER

CROSS-REFERENCE TO RELATED APPLICATIONS

The present invention relates to, and is entitled to the benefit of the earlier filing date and priority of, Application No. 60/537,888 filed on Jan. 22, 2004 and Application No. 60/538,242 filed on Jan. 23, 2004.

FIELD OF THE INVENTION

The present invention relates generally surgical fasteners, and more particularly surgical fasteners for use in attaching tissue to tissue, surgical component to tissue, and surgical component to surgical component.

BACKGROUND

An aneurysm is a ballooning of the wall of an artery resulting from the weakening of the artery due to disease or other conditions. Left untreated, the aneurysm will frequently rupture, resulting in loss of blood through the rupture and death.

Aortic aneurysms are the most common form of arterial aneurysm and are life threatening. The aorta is the main artery which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels to the kidneys, the renal arteries. Below the level of the renal arteries, the abdominal aorta continues to about the level of the fourth lumbar vertebrae (or the navel), where it divides into the iliac arteries. The iliac arteries, in turn, supply blood to the lower extremities and perineal region.

It is common for an aortic aneurysm to occur in that portion of the abdominal aorta between the renal arteries and the iliac arteries. This portion of the abdominal aorta is particularly susceptible to weakening, resulting in an aortic aneurysm. Such an aneurysm is often located near the iliac arteries. An aortic aneurysm larger than about 5 cm in diameter in this section of the aorta is ominous. Left untreated, the aneurysm may rupture, resulting in rapid, and usually fatal, hemorrhaging. Typically, a surgical procedure is not performed on aneurysms smaller than 5 cm as no statistical benefit exists to do so.

Aneurysms in the abdominal aorta are associated with a particularly high mortality rate; accordingly, current medical standards call for urgent operative repair. Abdominal surgery, however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the abdominal wall (i.e., abdominal aorta). A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, methods have been developed to attempt to treat an abdominal aortic aneurysm without the attendant risks of intra-abdominal surgical intervention. Although techniques have been developed that may reduce the stress, morbidity, and risk of mortality associated with surgical intervention to repair aortic aneurysms, none of the prior art systems that have been developed effectively treat the aneurysm and exclude the affected section of aorta from the pressures and stresses associated with circulation. None of the devices disclosed in the references provide a reliable and quick means to reinforce an aneurysmal artery, and none of the devices disclosed provide a surgical fastener possessing the advantages of the fastener of the present invention. In addition, all of the prior references require a sufficiently large section of healthy aorta abutting the aneurysm to ensure attachment of the graft. The proximal aortic neck (i.e., above the aneurysm) is usually sufficient to support a graft's attachment means. However, when an aneurysm is located near the iliac arteries, there may be an ill-defined neck or no neck below the aneurysm. Such an ill-defined neck would have an insufficient amount of healthy aortic tissue to which to successfully attach a graft. Furthermore, much of the abdominal aortic wall may be calcified making it extremely difficult to attach a graft thereto.

One of the problems associated with current surgical fasteners is that these fasteners are difficult to insert and advance during surgical procedures because these fasteners lack adequate support. Additionally, current fasteners often result is excess bleeding. There is a need to develop a fastener that is easier to advance and curtails the amount of bleeding during surgical procedures. None of the prior art systems provide a surgical fastener that achieves the advantages of the present invention.

Additional advantages of various embodiments of the invention are set forth, in part, in the description that follows and, in part, will be apparent to those of ordinary skill in the art from the description and/or from the practice of the invention.

SUMMARY

The present invention is directed to a surgical fastener for use during a surgical procedure for securing a first component to a second component. The surgical fastener secures a first component to a second component under a force. The surgical fastener has a first stressed configuration where the fastener is coupled to a restraining device that can be used to insert the surgical fastener into both components. After insertion, the restraining device can be removed resulting in a second unstressed configuration in which the surgical fastener has a substantially spiral shape on the outer side of both components. The surgical fastener is spring biased towards the middle thereby securing the two components together. The surgical fastener also includes a rib that extends along the longitudinal axis of the surgical fastener. The rib may facilitate more reliable insertion and more consistent advancement.

In accordance with an embodiment of the present invention, the surgical fastener may have a first configuration for inserting the surgical fastener through the second component and the first component, and a second configuration when the surgical fastener is in a secured position.

In accordance with another embodiment of the present invention, surgical fastener further comprises of at least one ring that is created by having a finger connect to the rib that runs along the longitudinal axis of the surgical fastener. The ring assembly may further include using different ring dimensions and spring characteristics. By adjusting the variables of the ring width and tension, the rings can help facilitate a more effective surgical fastener. For example, in one embodiment, to reduce the chance of substantive bleeding, the rings are cut in a manner that results in closure of the rings when the surgical fastener assumes its second or spiraled configuration. Additionally, instead of the surgical fastener being constructed from wire, it may now be laser cut from tubing; for example, laser cut Nitinol or cut by any suitable method.

Embodiments of the present invention disclose various improvements to the surgical fastener to assist in insertion and delivery of the surgical fasteners as well as reduce bleeding during surgical procedures.

Additional advantages of the invention will be set forth in part in the description that follows, and in part will be obvious from the description, or may be learned by practice of the invention. The advantages of the invention will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments of the invention and together with the description, serve to explain the principles of the invention. Where appropriate, the same reference numerals refer to the same or similar elements.

DETAILED DESCRIPTION OF EMBODIMENTS OF THE INVENTION

Reference now will be made in detail to the apparatus and methods consistent with implementations of the present invention, examples of which are illustrated in the accompanying drawings. The appended claims define the scope of the invention, and the following description does not limit that scope.

Figure 1:
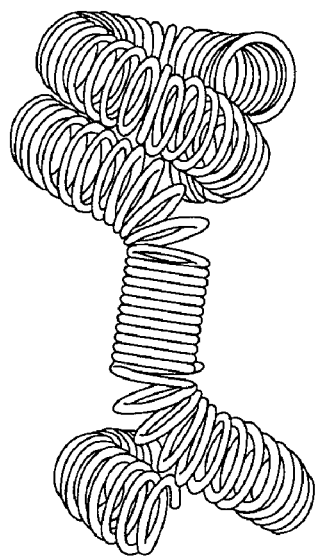
FIG. 1 is a schematic view of a surgical fastener according to the prior art.
Figure 2:
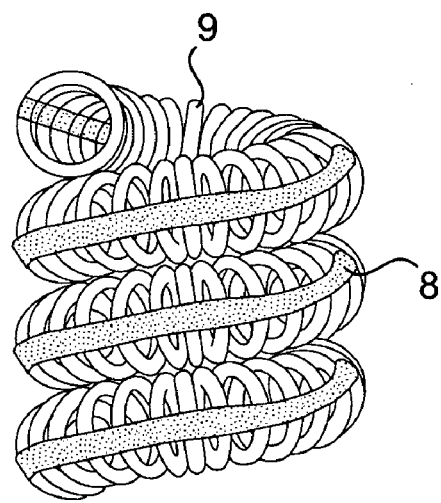
FIG. 2 is a schematic view of a surgical fastener according to an embodiment of the present invention in a relaxed coiled configuration.

FIG. 1 depicts a surgical fastener as described in U.S. Pat. Nos. 5,997,556; 6,248,118; and 6,520,974, herein incorporated in their entirety by reference.

FIGS. 2-8 illustrate a surgical fastener according to embodiments of the present invention. Surgical fastener 1 may be composed of any suitable material, such as, but not limited to, shape memory metal alloy wire or plastic, such as, but not limited to Nitinol, or any other suitable material. The material may include additional elements which affect the yield strength of the material or the temperature or other stimulus, including but not limited to electrical, magnetic, or aqueous at which particular pseudoelastic or shape transformation characteristics occur. The transformation temperature or stimulus may be defined as the temperature or stimulus at which a shape memory or plastic alloy finishes transforming from martensite to austenite upon heating or stimulus. The shape memory alloy preferably exhibits pseudoelastic (superelastic) behavior when deformed at a temperature slightly above its transformation temperature. At least a portion of the shape memory alloy is converted from its austenitic phase to its martensitic phase when the wire is in its deformed configuration. As the stress is removed, the material undergoes a martensitic to austenitic conversion and springs back to its original undeformed configuration. When the surgical fastener 1 is positioned within the tissue 5 in its undeformed configuration, a residual stress is present to maintain the tissue tightly together. In order for the surgical fastener 1 to retain sufficient compression force in its undeformed configuration, the surgical fastener 1 should not be stressed past its yield point in its deformed configuration to allow complete recovery of the wire to its undeformed configuration. The shape memory alloy is preferably selected with a transformation temperature suitable for use with a stopped heart condition where cold cardioplegia has been injected for temporary paralysis of the heart tissue (e.g., temperatures as low as 8-10 degrees Celsius). It is to be understood that the shape memory alloy may also be heat activated, or a combination of heat activation and pseudoelastic properties may be used, as is well known by those skilled in the art.

The surgical fastener 1 is distorted into a first configuration to allow it to be placed sequentially over or within a penetration apparatus, such as, but not limited to, an optical fiber, and inserted sequentially through a first component and a second component. The first component or second component may be a tissue, surgical component, or any combination, such as, but not limited to, a prosthetic graft and vessel or aortic wall. There are also many other potential uses for surgical fastener 1, including, but not limited to, hernia repair, bowel anastomosis, dissection of an artery, etc.

Surgical fastener 1 may be of about 0.0254 mm to about 2.54 mm diameter, such as, but not limited to, about 0.508 to about 1.524 mm diameter with a lumen of about 0.0254 mm to about 2.54 mm diameter, such as, but not limited to, about 0.127 to about 1.27 mm diameter.

According to an embodiment of the present invention surgical fastener 1 is a tubular structure and may comprise a rib 8 that may reduce compression, facilitate more consistent advancement, and may be of varying width. Rib 8 may be straight or helical, and may be integrated into, or form a wall of, surgical fastener 1, or may be disposed within the tubular structure or disposed on the exterior of surgical fastener 1. Surgical fastener 1 may also comprise at least one ring 9 attached to rib 8. At least one rib 8 and/or at least one ring 9 may extend beyond the tubular structure to assist in anchoring of surgical fastener 1 in the first and/or second component. At least one rib 8 and/or at least one ring 9 may contain a rough or serrated edge or edges to assist in anchoring of surgical fastener 1 in the first and/or second component. Surgical fastener 1 may also comprise tip 10, which may be disposed on the leading or trailing end portion of surgical fastener 1.

Figure 3:
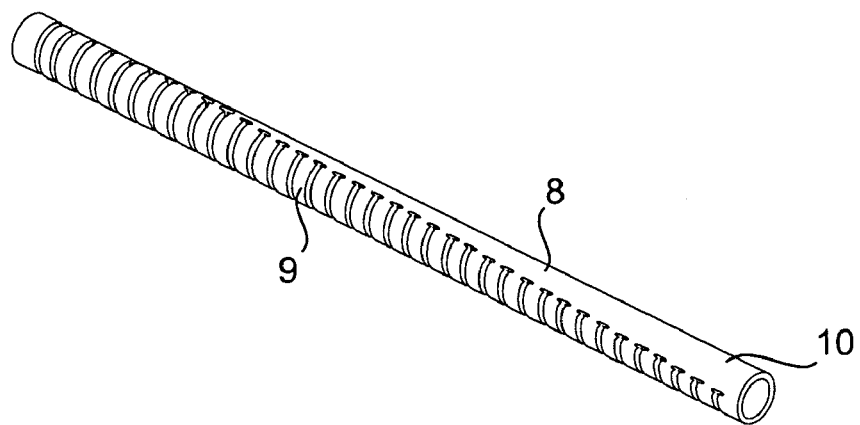
FIG. 3 is a schematic view of a surgical fastener according to an embodiment of the present invention in a stressed straight configuration showing a spiral rib.
Figure 4:
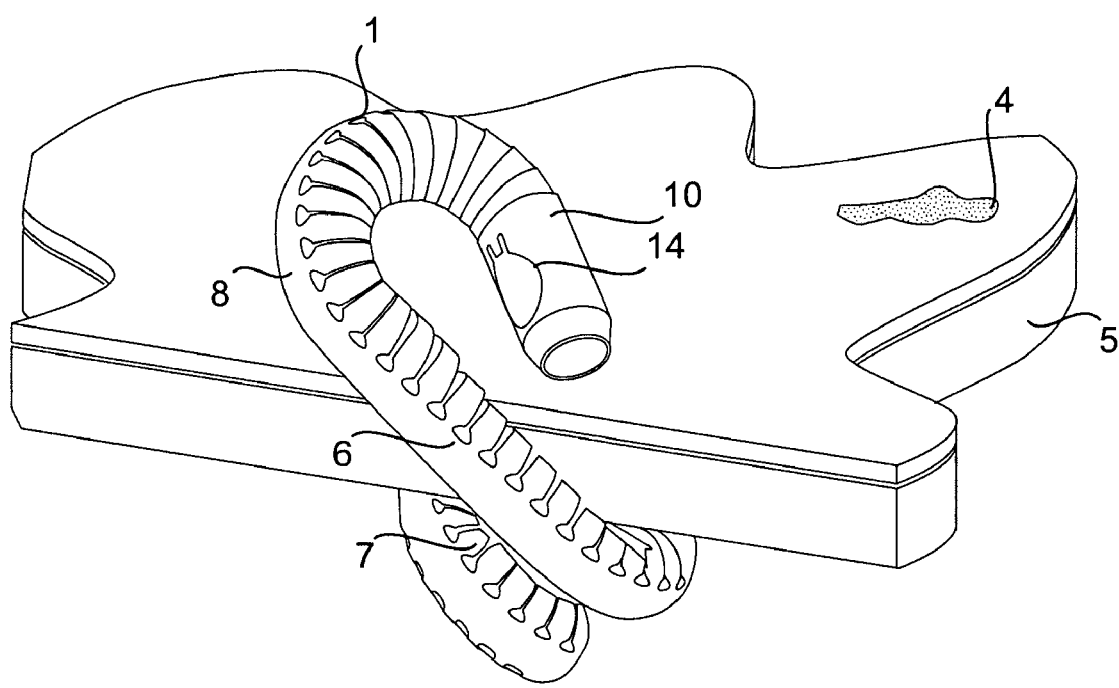
FIG. 4 is a schematic view of a surgical fastener according to an embodiment of the present invention attaching a surgical component to tissue.
Figure 5:
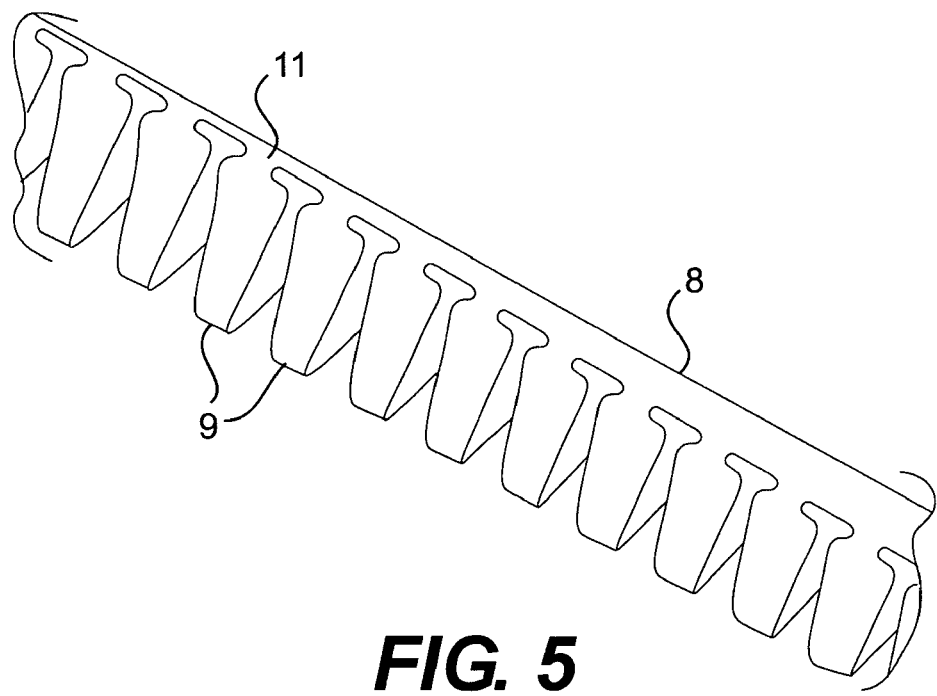
FIG. 5 is a schematic view of the rings of the surgical fastener according to an embodiment of the present invention.
Figure 6:
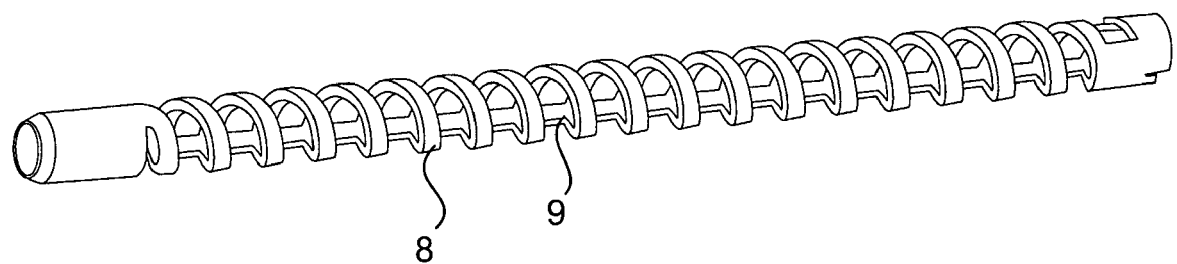
FIG. 6 is a schematic view of the rings of the surgical fastener according to an embodiment of the present invention.
Figure 7:
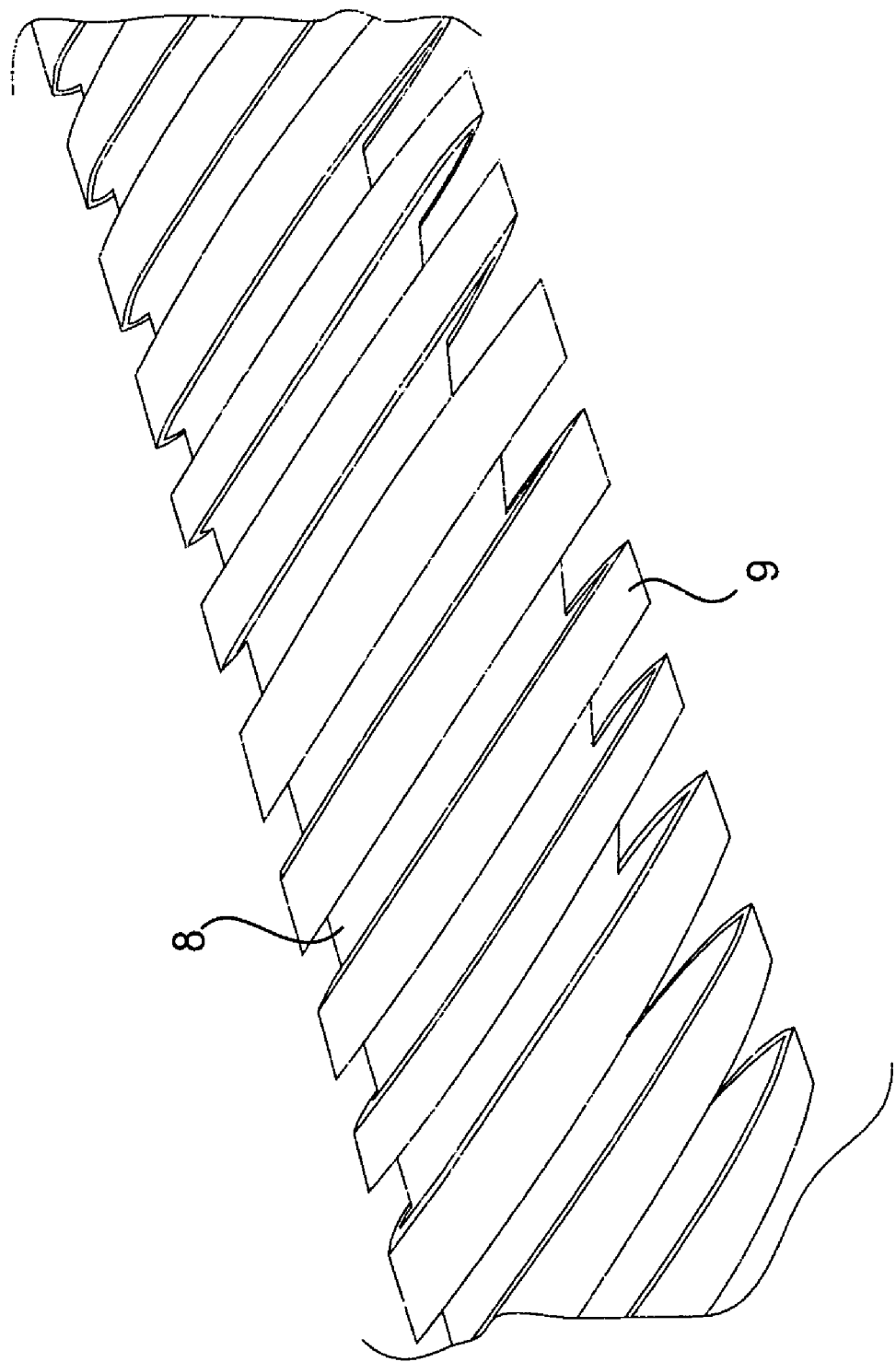
FIG. 7 is a schematic view of the rings of the surgical fastener according to an embodiment of the present invention.
Figure 8:
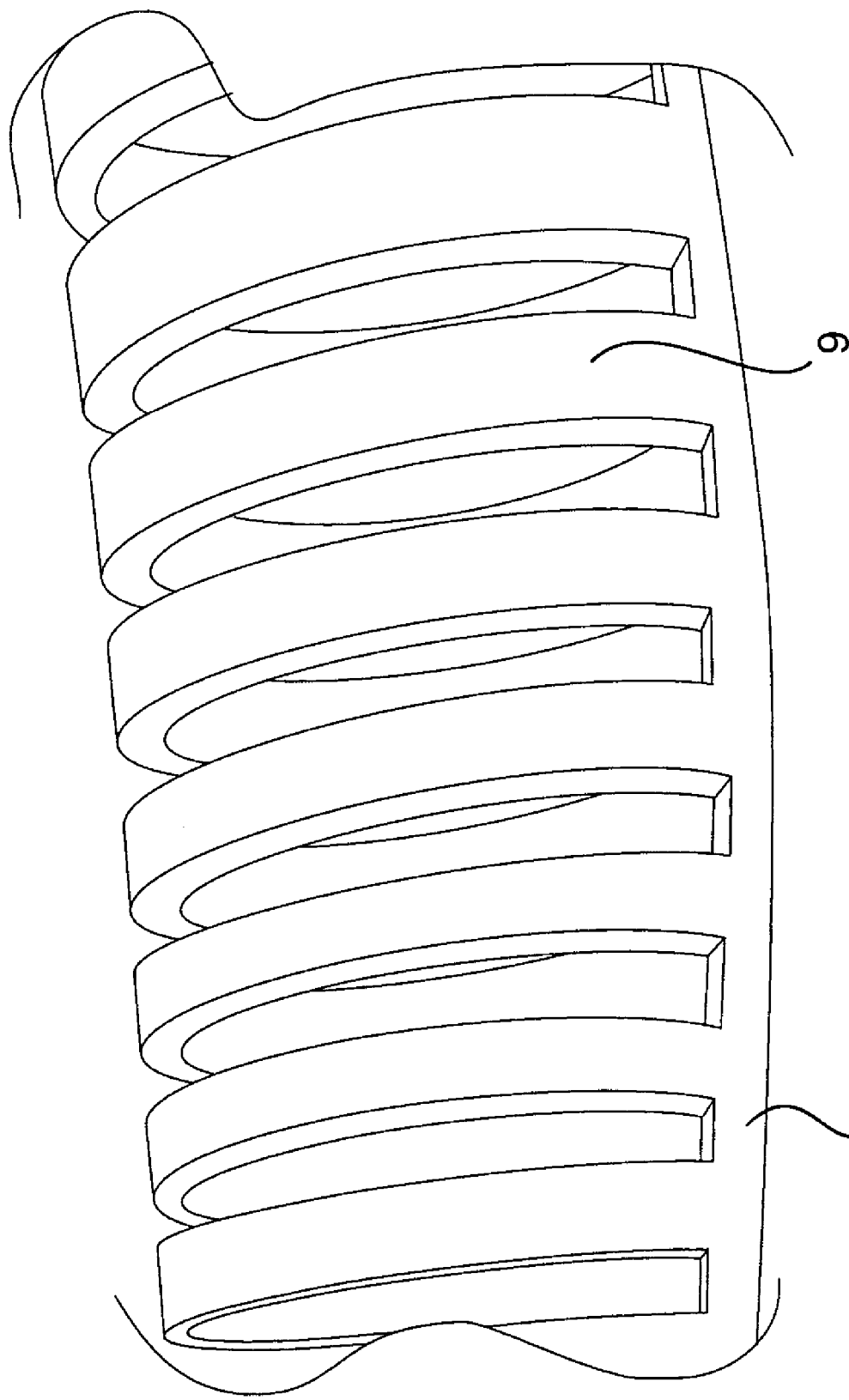
FIG. 8 is a schematic view of the rings of the surgical fastener according to an embodiment of the present invention

According to a method of use of an embodiment of the present invention, and referring to FIGS. 3 and 4, surgical fastener 1 is shaped into a primary coil (that may be, but is not limited to, approximately between 0.0254 mm and 2.54 mm in diameter) that is, in turn, set into a secondary coil, by heat or any other suitable means (that may be, but is not limited to, approximately between 0.0254 mm and 2.54 mm in diameter). As described previously, the surgical fastener 1 is deflected into a single coil and loaded onto or around a penetration apparatus, such as, but not limited to, an optical fiber; the penetration apparatus is positioned adjacent to a first component, such as, but not limited to, a prosthetic graft, a penetration means, such as, but not limited to, a Holmium laser is pulsed through the fiber allowing the laser energy to create a hole through the prosthetic graft and a second component, such as, but not limited to, an adjacent aorta as the fiber and overlying surgical fastener 1 are advanced; the optical fiber is then withdrawn and the fastener 1 then assumes its first coiled coil configuration. FIG. 4 depicts the coiled coil that has been inserted from within the aortic lumen through a prosthetic graft 4 and an adjacent vessel wall 5. One of the primary coils has been left positioned within the vessel lumen, a portion of the coiled coil 6 traverses the prosthetic graft and vessel and the remainder of the coiled coil 7 (secondary coil) is positioned adjacent to the outside of the vessel in an area called the periadvential tissue. Once in position, tissue ingrowth into the interstices of the coils may provide further resistance to surgical fastener 1 dislodgment. In one embodiment, the primary coil contains only one coil so as to minimize the amount of fastener that is left inside the vessel. The secondary coil can contain more coils because it is located outside of the vessel.

According to another embodiment of the present invention, surgical fastener 1 may be comprised of a metal alloy, plastic or any other suitable material that may be set in a first configuration and distorted into a second configuration without losing its ability to resume its first configuration when a distorting force is removed. FIG. 3 shows a rib 8 with rings 9 attached. The rib 8 can be of varying width and can be helically positioned, as shown, or it can be straight.

FIGS. 5-9 show views of various embodiments of rib 8 and attached rings 9. Rings 9 can be cut in any configuration; specifically the width may vary, the space between ribs 8 may vary, and the bias at which ribs 8 are cut may vary. The desired ring 9 configurations, as shown, may be broader near rib 8 and narrower at the portion opposite rib 8 to enhance closure of rings 9 when surgical fastener 1 is in its second, or relaxed coiled coil configuration. The desired bias at which rings 9 are cut may facilitate the closure of rings 9, although there could be instances when the bias could be different in order to more readily achieve other goals such as facilitating resistance to distracting forces (hernia repair for instance). By altering some of these variables, such as, but not limited to, surgical fastener 1 tube thickness and or diameter, rib 8 width, ring 9 dimensions, the bias at which rings 9 are cut and the way the secondary coil may be heat set i.e. right-handed or left-handed, the force ("pinch force") required to distract one secondary coil from its adjacent coil can be increased or decreased. Connection 11 of ring 9 to rib 8 may be of any suitable configuration and width. Connection 11 of the embodiment depicted in FIG. 4 has a "bow tie" shape and selected for its ability to facilitate ring 9 closure and to reduce rib 8 and ring 9 interface stress.

Figure 9:
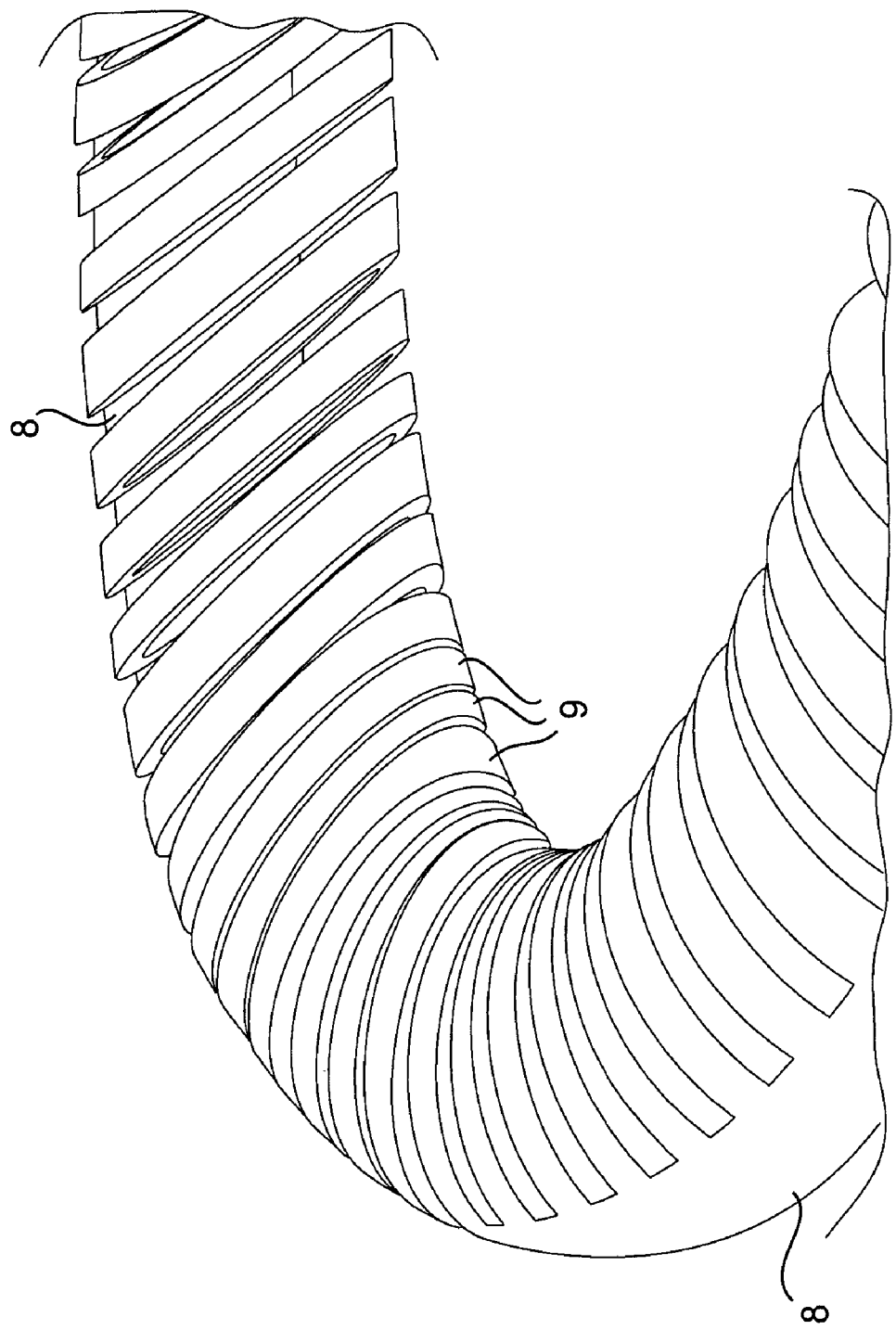
FIG. 9 is a schematic view of a partially coiled surgical fastener according to an embodiment of the present invention.

FIG. 9 shows an embodiment of the present invention in a coiled configuration illustrating rib 8 and a plurality of rings 9 attached to rib 8 and compressed into a closed configuration 12. Combined with rib 8 opposite the radius of the turn, this structure reduces the likelihood of bleeding through the interstices of rings 9. Because the space between ribs 8 may be large, it may be desirable to dispose or attach a foam or sponge, or any other suitable material, in these spaces in order to allow movement of rings 9 when a penetration apparatus is bent or removed but also provide a barrier to bleeding through the spaces between rings 9. Rings 9 can be cut at any width and/or any angle and the distance between rings 9 can vary as well. There can also be more than one rib 8.

Figure 10:
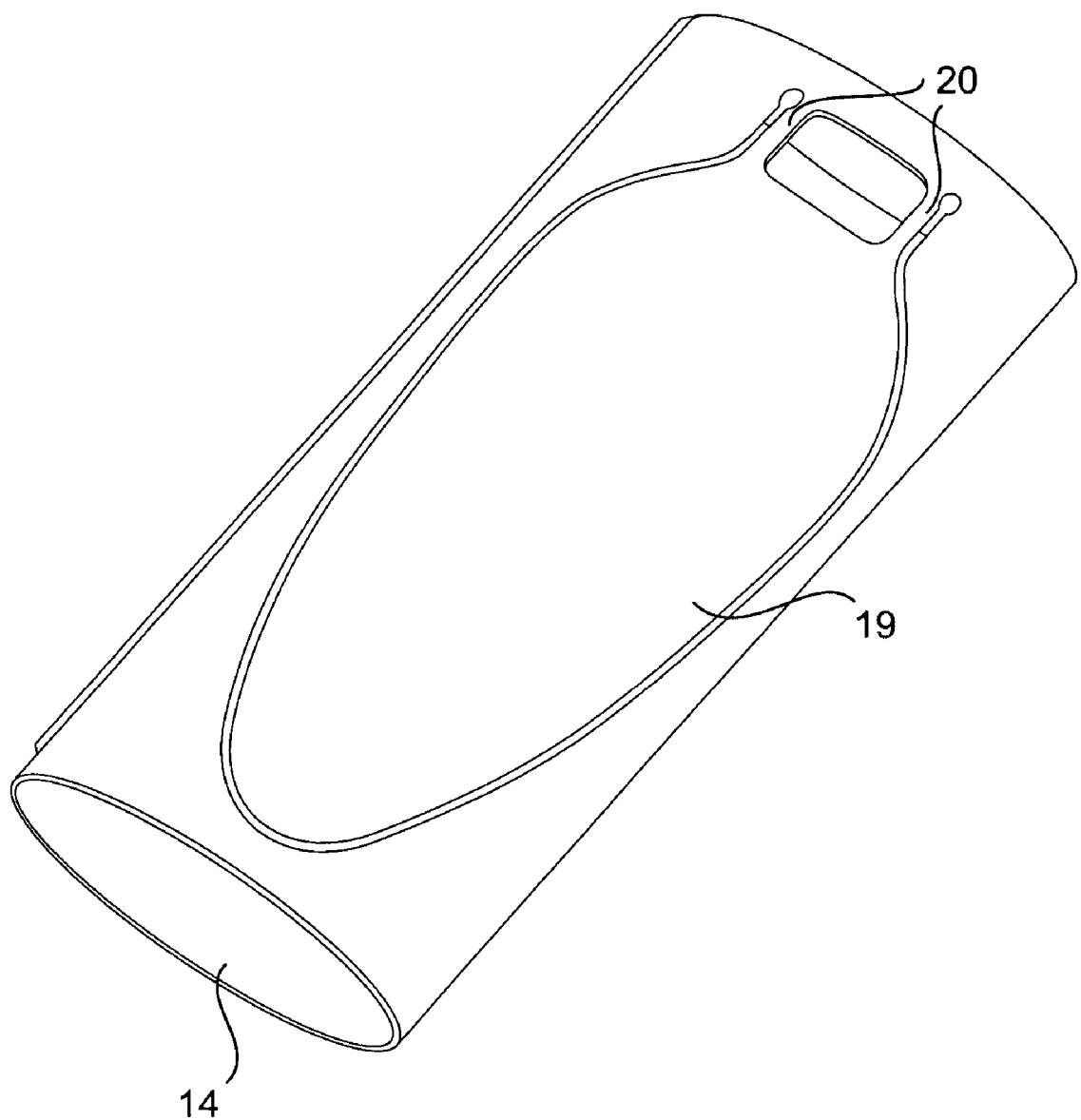
FIG. 10 is a schematic view of an occlusive device according to an embodiment of the present invention.

FIG. 10 shows the occlusive device 14. A number of different occlusive devices 14 may be used as previously described in U.S. patent application Ser. No. 10/667,521, herein incorporated in its entirety by reference. In one embodiment occlusive device 14 is comprised of a single flap valve 19 with a double hinge 20 that may be laser cut at the same time rings 9 are cut as part of surgical fastener 1. Occlusive device 14 may positioned at the leading edge of surgical fastener 1 but, regardless of its design, may also be located at the trailing edge or anywhere between the two ends of surgical fastener 1, or in a tip 10 attached to surgical fastener 1. In one embodiment shown in FIG. 10, occlusive device 14 is positioned as if it were being held open by a penetration device, such as, but not limited to, an optical fiber passing through its lumen. Occlusive device 14 may be composed of any suitable material, such as, but not limited to, shape memory metal alloy wire or plastic, such as, but not limited to Nitinol, or any other suitable material.

Figure 11:
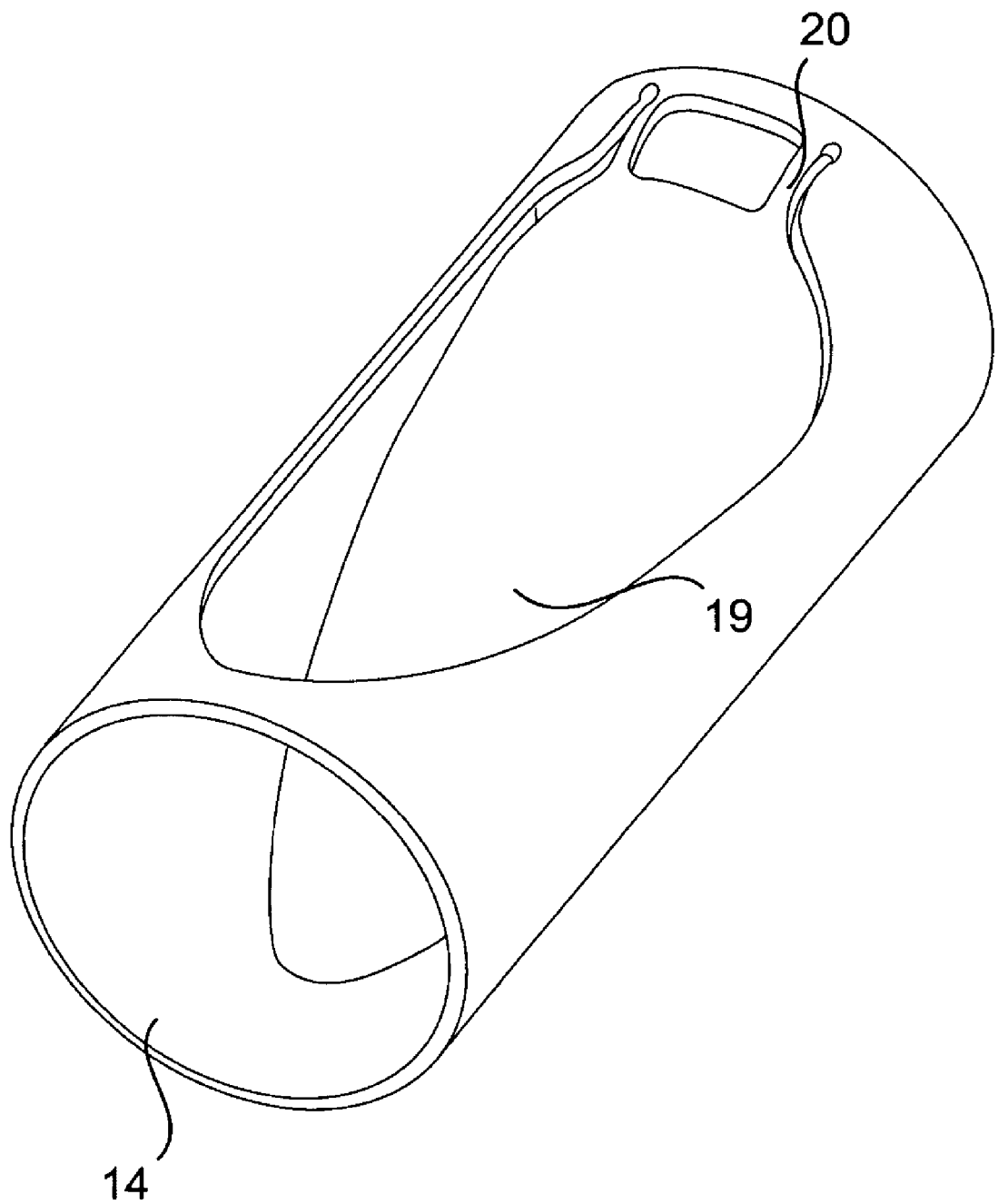
FIG. 11 is a schematic view of an occlusive device according to an embodiment of the present invention.

FIG. 11 depicts the occlusive device 14 in its relaxed state once the penetration apparatus has been removed from the lumen of the tubing 15.

Figure 12:
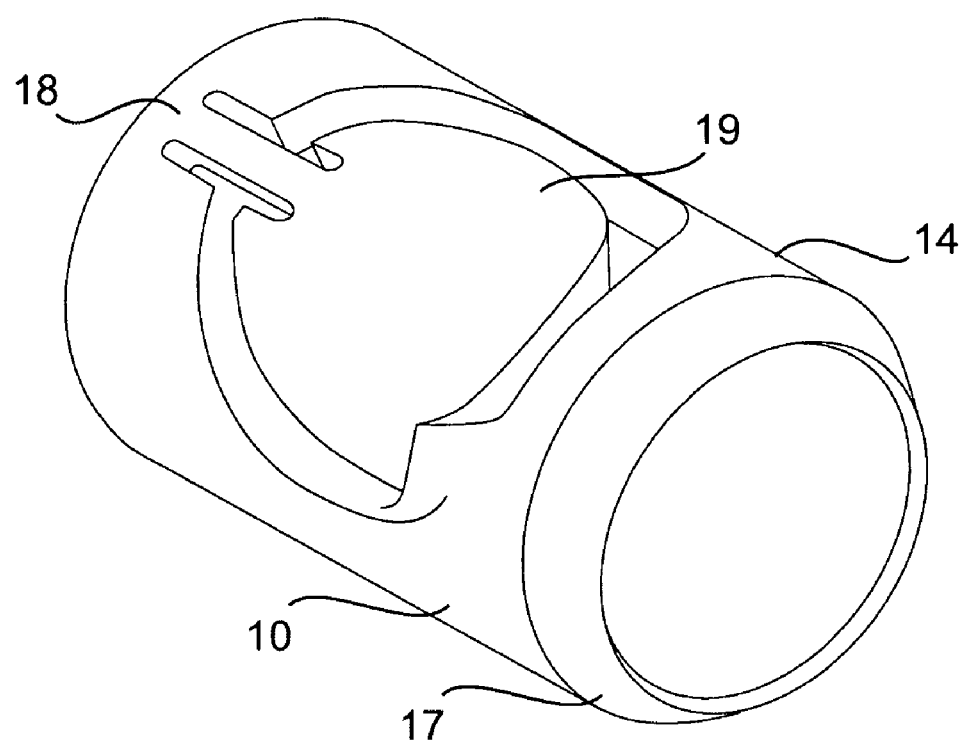
FIG. 12 is a schematic view of an occlusive device according to an embodiment of the present invention.

FIG. 12 depicts tip 10 with a taper 17. The occlusive device 14 consisting of a single flap valve 19 with a single hinge 18. The taper 17 and occlusive device 14 can be each be manufactured separately and combined with the staple described above or, in the preferred iteration, the staple, taper tip and occlusive mechanism can be cut from the same piece of material.

Figure 13:
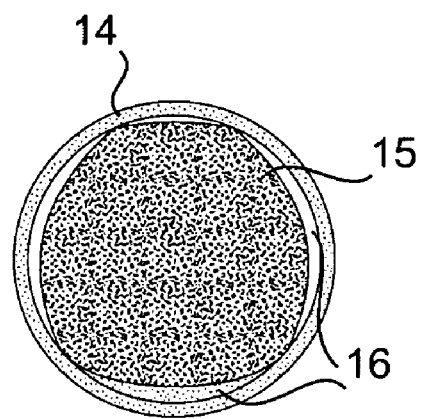
FIG. 13 is a schematic view of an occlusive device according to an embodiment of the present invention.

FIG. 13 shows an end view with the occlusive device 14 in its relaxed state occluding almost all of the lumen of surgical fastener 1. Only small spaces 16 may remain that could allow passage of blood through surgical fastener 1 lumen.

Numerous characteristics and advantages have been set forth in the foregoing description, together with details of structure and function. The novel features are pointed out in the appended claims. The disclosure, however, is illustrative only, and changes, may be made in detail, especially in matters of shape, size, and arrangement of parts, within the principle of the invention, to the full extent indicated by the broad general meaning of the terms in which the appended claims are expressed.

What is claimed is:

1. A surgical fastener having a first and a second end for securing at least two surfaces together comprising,
    a first configuration wherein said fastener is coupled to a restraining device holding said fastener,
    a second configuration wherein said fastener is released from said restraining device, said second configuration having a substantially spiral shape,
    wherein said second configuration is spring biased along an axis perpendicular to said at least two surfaces that are being secured together, wherein said first end and said second end are spring biased towards each other, a rib extending along the longitudinal axis of said surgical fastener, at least one ring having a top end, a bottom end, and a middle portion disposed between said top end and said bottom end wherein at least one of said top end and said bottom end are in communication with said rib, and wherein said ring has a width that is generally broader at said top or said bottom end when compared to said middle portion.

2. The surgical fastener of claim 1, comprising a connection, wherein said connection is disposed between said rib and at least one of said top end and said bottom end.

* * * * *